(12) United States Patent
Ebert et al.

(10) Patent No.: US 6,952,258 B2
(45) Date of Patent: *Oct. 4, 2005

(54) WAFER CHUCK WITH INTEGRATED REFERENCE SAMPLE

(75) Inventors: Martin Ebert, Fremont, CA (US); Thomas Traber, Dublin, CA (US)

(73) Assignee: Therma-Wave, Inc., Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/843,159

(22) Filed: May 11, 2004

(65) Prior Publication Data

US 2004/0207838 A1 Oct. 21, 2004

Related U.S. Application Data

(63) Continuation of application No. 10/050,653, filed on Jan. 14, 2002, now Pat. No. 6,757,059.
(60) Provisional application No. 60/287,360, filed on Apr. 30, 2001, and provisional application No. 60/336,515, filed on Nov. 1, 2001.

(51) Int. Cl.$^7$ ................................................ G01N 21/01
(52) U.S. Cl. ....................................................... 356/244
(58) Field of Search .......................... 356/237.1–237.5, 356/244–246; 250/225

(56) References Cited

U.S. PATENT DOCUMENTS

| | | | |
|---|---|---|---|
| 5,608,526 A | 3/1997 | Piwonka-Corle et al. | ... 356/369 |
| 5,924,058 A | 7/1999 | Waldhauer et al. | ......... 702/170 |
| 6,278,519 B1 | 8/2001 | Rosencwaig et al. | ....... 356/369 |
| 6,621,578 B1 | 9/2003 | Mizoguchi | ................... 356/369 |
| 2001/0010579 A1 | 8/2001 | Nishi | .......................... 355/67 |

*Primary Examiner*—Michael P. Stafira
(74) *Attorney, Agent, or Firm*—Stallman & Pollock LLP

(57) ABSTRACT

The subject invention relates to a wafer stage, such as may be used in optical wafer metrology instruments. The stage contains a wafer-chuck that can be connected to translation stages for the purpose of clamping and translating the wafer so that a plurality of sites on the wafer surface may be measured. The chuck includes a holder for mounting a reference sample. The holder is movable between a retracted position where the reference sample is held below the chuck surface and an extended position, such as where the surface of the reference sample is co-planar with the wafer surface. Therefore the holder may be installed within the area of the chuck that is utilized for wafer clamping. By this arrangement, the size of the wafer translation system can be reduced minimizing the stage travel and enabling increased spatial resolution, increased wafer throughput and reduced capital equipment and operating costs.

26 Claims, 4 Drawing Sheets

WAFER CHUCK WITH INTEGRATED REFERENCE SAMPLE

The present application is a continuation of U.S. patent application Ser. No. 10/050,653, filed Jan. 14, 2002, and now U.S. Pat. No. 6,757,059, which claims priority to the U.S. Provisional Patent Application Ser. No. 60/287,360 filed Apr. 30, 2001, and Ser. No. 60/336,515 filed Nov. 1, 2001, both of which are incorporated herein by reference.

TECHNICAL FIELD

The subject invention relates to optical metrology devices which include a movable stage for rastering a wafer with respect to a measuring probe beam. More specifically, the invention relates to a stage which includes a system for mounting a reference chip within the footprint of the wafer thereby reducing the amount of stage travel necessary to measure both the wafer and the reference chip.

BACKGROUND OF THE INVENTION

Optical metrology instruments require periodic monitoring and calibration. The output intensity of the light sources, the nature and extent of solarization of the optical components, chemical contamination of the optical surfaces and the alignment of the system optics can all vary with system operating time. An instrument's performance must be regularly monitored to verify that the system continues to meet operational specifications and that measurements are performed with the required precision and accuracy. Frequently, this is accomplished with the aid of a reference sample. A reference sample is a well-characterized specimen with known and temporally stable optical properties. Any variation in the measurement of the reference sample optical response is indicative of a variation in performance of the instrument. It is the periodic measurement of the reference sample that indicates performance problems and the requirement for maintenance or re-calibration.

Optical wafer metrology systems are characteristically configured with the wafer surface approximately coincident with the focal plane of the optical system. The focal plane is flat and perpendicular to the plane of incidence of the probe beam (typically defined as the x-y plane). The vertical or z position of the wafer should coincide with the focus position of the probing beam.

High-resolution "small spot-size" optical wafer metrology tools illuminate a small portion of the wafer surface at the focal position and monitor the change in one or more properties of the reflected light caused by the interaction with the sample surface. Characteristically, measurements are made sequentially as a translating wafer stage moves the wafer surface "through" the illuminated region. Conventional wafer "mastering" or translation protocols include both bi-linear, x-y translation and single-axis translation in combination with z-axis rotation. The stage system can also include z-axis movement for raising and lowering the wafer surface to achieve focus.

In the prior art it has been desirable to place the reference sample in the focal plane. If the reference surface is physically located within the same plane as the wafer surface, no substantial refocusing of the optical system is required during measurement of the standard sample. For systems employing x-y translation stages the reference sample is typically attached to the wafer chuck at the corner of the stage where it does not interfere with wafer measurements. For systems employing z-axis rotation stages, restrictions posed by rotation symmetry, the location of auxiliary metrology instrumentation and the location and design of the wafer handling equipment make locating the reference sample more difficult. Even when a suitable location can be identified this often requires a more expensive, long-travel stage to be used so that the reference sample can be moved to the measurement position. These factors increase both the complexity of the instrument and its cost and size.

Accordingly it would be desirable to locate the reference sample on the wafer chuck within the wafer footprint. This offers two important advantages. First, the stage-travel requirements are determined solely by the wafer dimensions. Therefore minimum form-factor wafer-translation systems can be employed. Second, a major limitation of the prior-art approach is eliminated permitting the use of compact wafer-translation systems having rotary stages. In particular, the prior approach of placing a reference chip outside a circular chuck and connected to the chuck cannot be implemented in a rotational system where an external pin lifter mechanism is used to raise wafer. As can be appreciated, if the reference chip extended beyond the circumference of the chuck, it would prevent the chuck from rotating since it would intersect with the pins of the wafer lifter. Placing the reference sample within the footprint of the chuck allows an external pin lifter to be used with a rotational chuck.

BRIEF SUMMARY

The subject invention relates to an apparatus for holding and translating a wafer in an optical wafer metrology tool. The apparatus incorporates a wafer-chuck that is attached to and combined with a wafer translation system. The apparatus further includes a holder for a reference specimen. The holder is installed within the body of the wafer-chuck within the area of the chuck used for wafer clamping. The holder is movable between a retracted position where the reference sample is below the chuck surface, and an extended position where the reference sample is substantially coincident with the wafer position. During wafer metrology the holder is maintained in the retracted position. Measurement of the reference sample is made with the wafer removed and the holder maintained in the extended position.

Locating the reference specimen within the area of the chuck used for wafer clamping enables an economy of design. The required range of stage-travel is set by the wafer dimensions. This admits the use of extremely short-travel translation stages to access large wafer areas. For example, the entire surface of a 300 mm diameter wafer can be accessed using a single 270 degree rotary-stage in combination with two ±75 mm linear-travel stages, e.g. ±75 mm of travel in the x direction and ±75 mm in the y direction. The economy of motion enables increased accuracy of wafer positioning and increased wafer-throughput at reduced cost.

DETAILED DESCRIPTION

Figure 1:
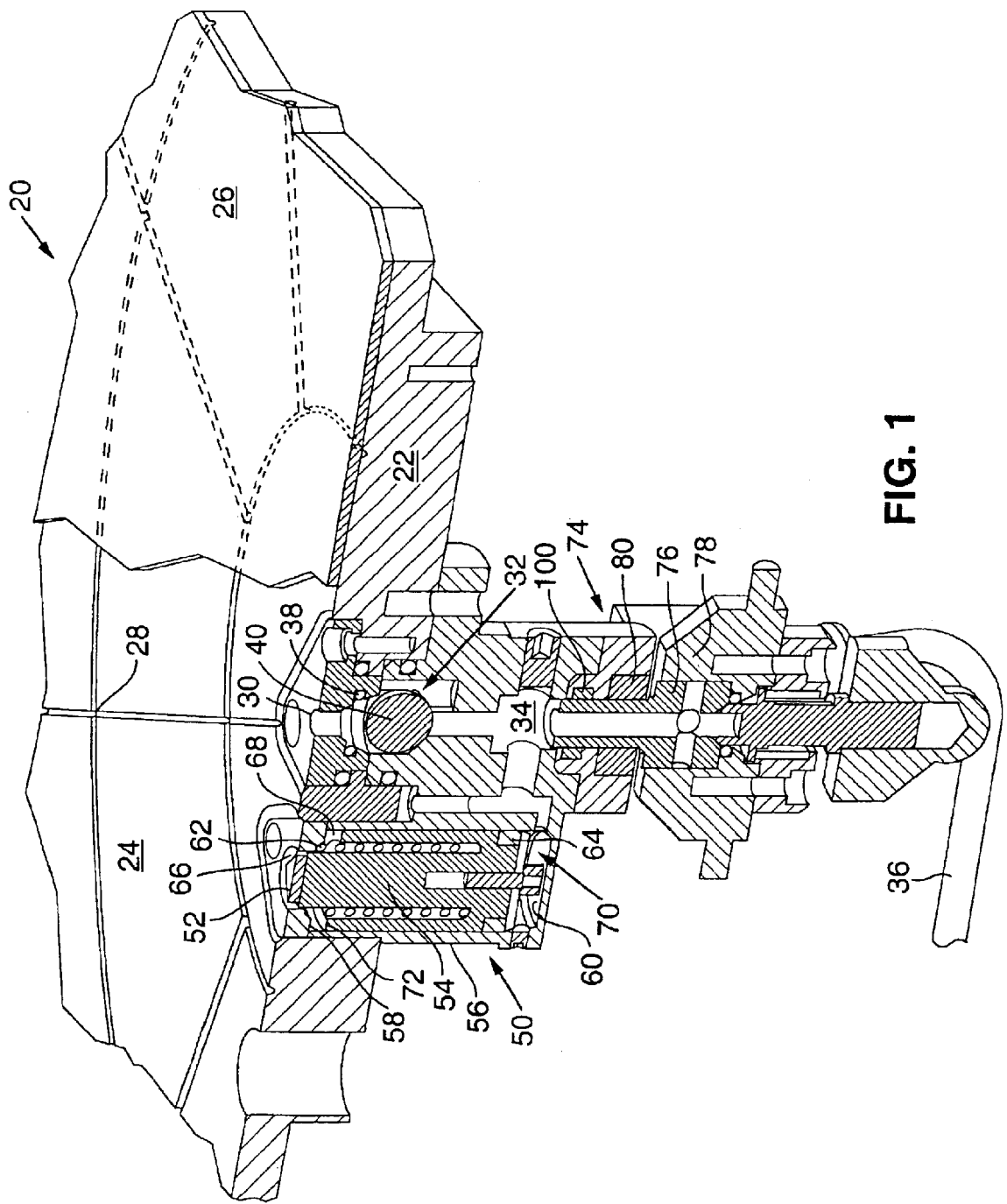
FIG. 1 is a cross-sectional view of the vacuum chuck with the holder in the retracted position.
Figure 2:
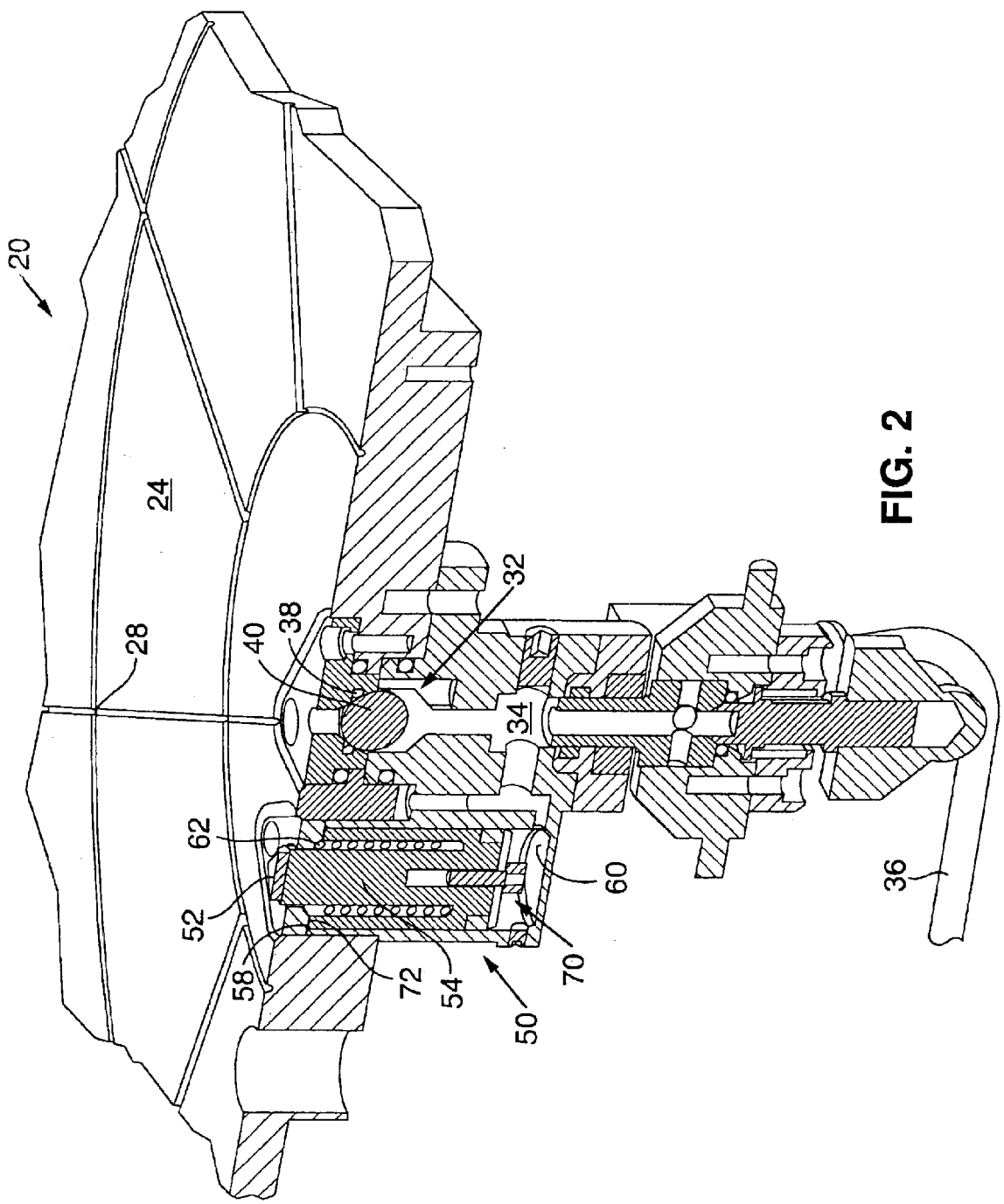
FIG. 2 is a cross sectional view of the vacuum chuck with the holder in the extended position.

FIGS. 1 and 2 are cross-sectional schematics of a preferred embodiment of the wafer-chuck 20 showing the position of holder 50 during wafer metrology and measurement of the reference sample. FIG. 1 illustrates the configuration of the chuck employed in the metrology of wafer 26. FIG. 2 illustrates the configuration of the chuck during measurement of reference sample 52.

Wafer-chuck 20 includes a platform 22 for supporting and clamping a wafer 26. Platform 22 includes a support surface 24 for locating and supporting the wafer. The locating surface further includes a series of intersecting radial and circular channels 28 which may be connected to a vacuum supply via orifice 30, check valve assembly 32, manifold 34 and supply line 36. When supply line 36 is connected to a vacuum system, surface 22, channels 28, orifice 30, check-valve assembly 32, manifold 34 and supply line 36 comprise a vacuum wafer-chuck. In the preferred embodiment supply line 36 may be alternately connected to a vacuum system, a pressure relief-valve or a source of high-pressure gas.

The chuck further includes holder 50 for supporting and clamping reference sample 52. Holder 50 includes a reference sample 52, mounted to a spring-loaded piston assembly 54 that is free to move within cylinder 56 between a retracted and an extended position. The cylinder 56 includes upper 58 and lower 60 locating surfaces. Piston assembly 54 further includes a seal 64 that divides cylinder 56 into upper 68 and lower 70 hydraulic chambers. The lower hydraulic chamber is connected to manifold 34. The upper hydraulic chamber is connected to the surface 24 of platform 22 through orifice 66. A coil spring 62 is also provided to bias the holder into the retracted position.

FIG. 1 illustrates wafer-chuck 20 with holder 50 in the retracted position, the configuration used in wafer metrology, wherein spring 62 locates piston 54 at lower locating surface 60. In this position reference sample 52 is below the surface 24 of platform 22 and wafer 26 is clamped to platform 22.

FIG. 2 illustrates wafer-chuck 20 with holder 50 in the extended position, the configuration used for measurement of reference sample 52, wherein spring 62 is compressed and the piston 54 is driven upwards so that the upper locating surface 58 abuts the surface of shelf 72. In this position reference sample 52 is located at the measurement position, e.g. the upper surface is substantially co-planar with the upper surface of the wafer 26 as illustrated in FIG. 1.

Supply 36, manifold 34, check valve 32, piston 54, seal 64 and spring 62 comprise a hydro-mechanical actuation mechanism for moving holder 50 between the extended and retracted positions. Connecting supply 36 to a source of high-pressure gas causes holder 50 to move to the extended position. Initial pressurization of manifold 34 produces a differential pressure across ball 40 raising the ball and pressing it against seal 38 sealing check valve 32. With check-valve 32 sealed, manifold 34 and lower hydraulic chamber 70 fill with high-pressure gas. The pressurization of lower hydraulic chamber 70, compresses spring 62 raising piston 54 to the point where the piston locates at upper locating surface 58. In this position reference sample 52 is substantially at the measurement position, e.g. substantially the same position as the wafer illustrated in FIG. 1. This is the configuration illustrated in FIG. 2.

The holder is moved to the retracted position by connection of supply line 36 to a pressure relief valve which vents lower hydraulic chamber 70 and manifold 34. In this configuration, spring 62 forces the piston 54 against lower locating surface 60, and the holder is maintained in the retracted position with reference sample 52 below the surface 24 of platform 22. In the absence of pressurization of manifold 34, ball 40 moves downward, away from seal 38 opening check-valve 32 and connecting manifold 34 to channels 28 through orifice 30. With holder 50 in the retracted position wafer 26 can be located on surface 24 of platform 22 and clamped by connecting supply 36 to a vacuum system. In this configuration channels 28 are evacuated and the differential pressure established across the wafer 26 clamps wafer 26 to surface 24 of platform 22. This is the configuration illustrated in FIG. 1.

In the preferred embodiment illustrated in FIGS. 1 and 2 manifold 34 is connected to supply line 36 through a rotary bearing assembly 74. Assembly 74 consists of a fixed hollow shaft 76 mounted in a housing 78 that connects to supply line 36, and a rotary bearing 80 mounted within the body of manifold 34, which is fixed to platform 22. Bearing assembly 74 is arranged such that a hermetic rotary seal 100 is formed between the exterior surface of the hollow shaft and the inner surface of the rotating manifold. In the preferred embodiment, bearing system 74 also serves as a thrust bearing and supports the weight of platform 22. In this fashion platform 22 may be rotated about hollow shaft 76 while supply line 36 remains fixed and connects, through bearing assembly 74, manifold 34 to a vacuum system, a pressure-relief valve or a source of high-pressure gas.

It should be noted that in the preferred embodiment, a single fluid line 36 is used to supply vacuum to the chuck surface to "clamp" down the wafer and to provide the pressure to raise of the reference chip. This dual function is important since access to the rotating stage is limited to the rotation axis of the system.

Figure 3:
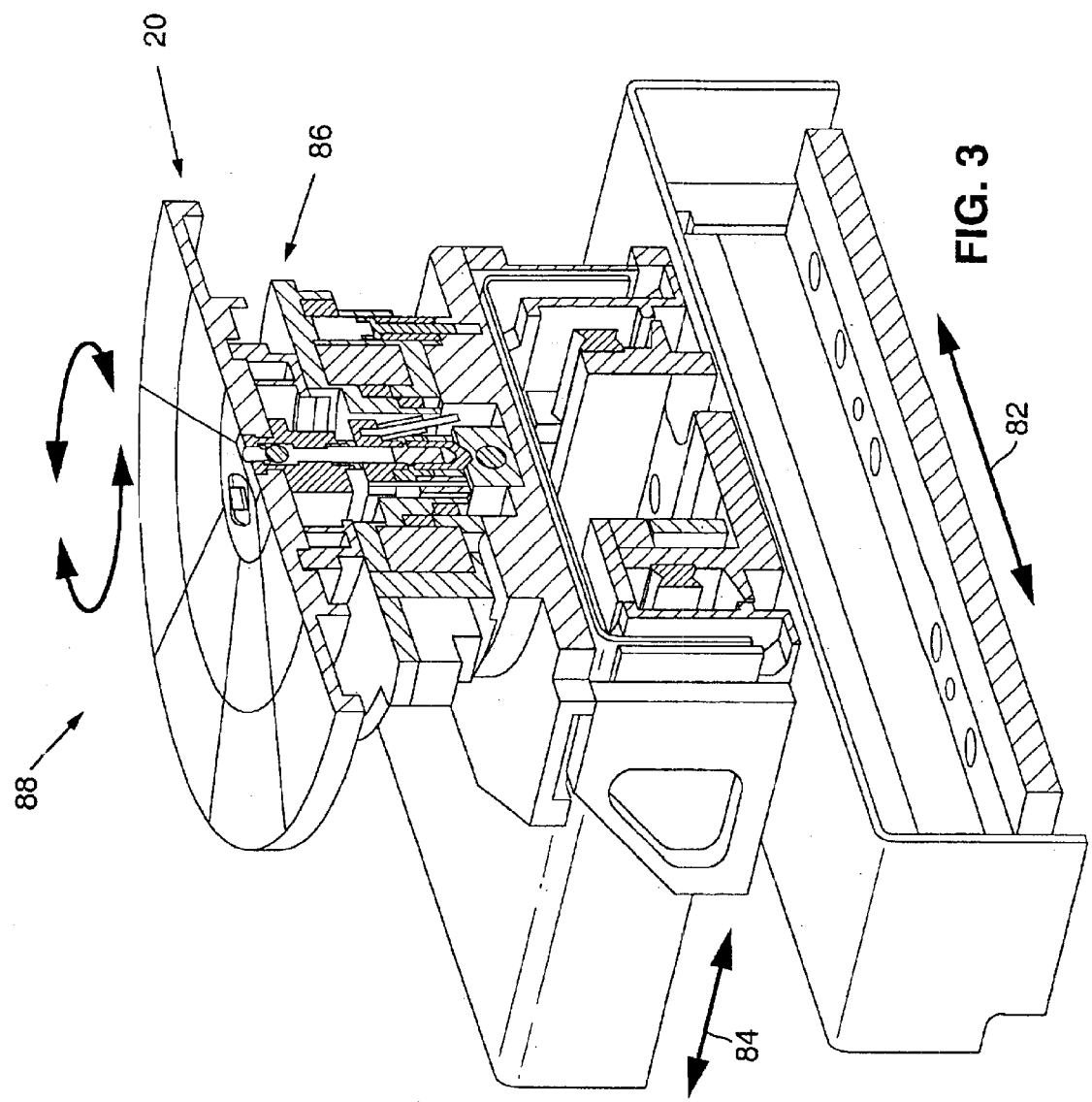
FIG. 3 is a cross-sectional view of a preferred embodiment of the wafer translation system.

FIG. 3 illustrates a preferred embodiment of a three-axis wafer-translation system 88 incorporating the wafer-chuck 20 shown in FIGS. 1 and 2 and described in the preceding discussion. Translation system 88 is comprised of wafer-chuck 20, rotary stage 86 and linear translation stages 82 and 84. Stages 82 and 84 are configured to provide translation in orthogonal directions within the x-y plane. Rotary stage 86 is arranged to provide rotation about the z-axis (perpendicular to the x-y plane). In the preferred embodiment, the rotary stage has 360 degrees of rotation. In addition, a mechanism (not shown) for raising and lowering the stage system in the vertical, z-axis is provided to permit the wafer to be brought into the focal plane.

As illustrated in the FIG. 3, the use of holder 50 permits the reference sample 52 to be located within the footprint of the wafer. This allows a minimum form-factor platform to be employed with dimensions determined by the wafer size.

Figure 4:
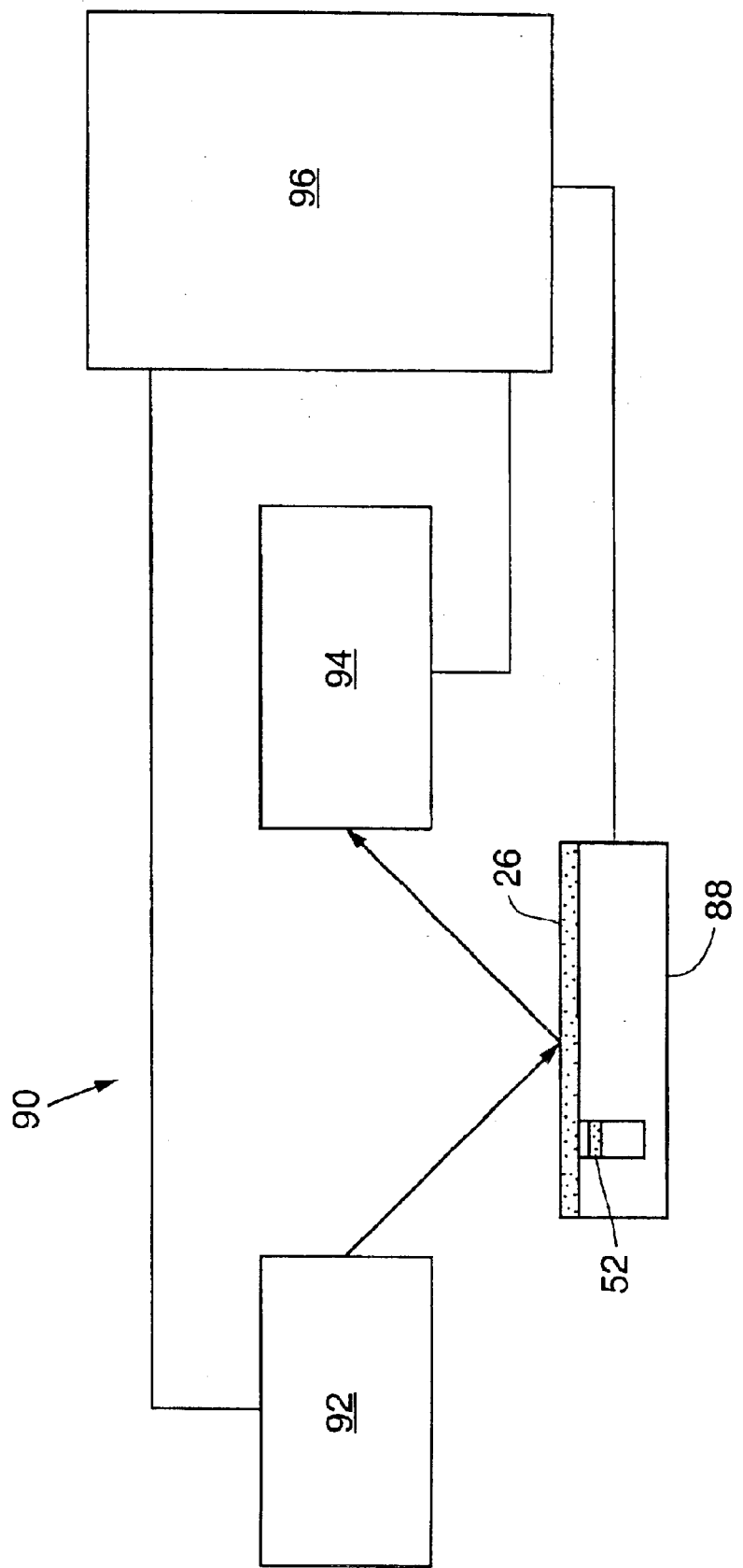
FIG. 4 is a schematic illustration of an optical metrology tool incorporating the wafer translation system.

FIG. 4 illustrates a preferred embodiment of the wafer translation system 88 incorporated in an optical metrology system 90. Optical metrology system 90 is configured to derive the characteristics of sample 26 by measurement and analysis of the changes in the incident illumination produced by reflection from and interaction with the sample 26. Optical metrology system 90 includes an illuminator 92, wafer translation system 88, sample 26, reference sample 52, detector 94 and processor 96.

Optical metrology system 90 may employ a plurality of measurement techniques either alone or in combination and including detection of the change in amplitude and the change in polarization state of the incident illumination upon reflection from and interaction with sample 26. Further these measurements may be made using both bright-field (e.g. reflectometry) and dark-field (e.g. scatterometry) detection strategies at a single wavelength, or at a plurality of wavelengths. Consequently, illuminator 92 and detector 94 may include one or more instruments selected from the group consisting of reflectometers, ellipsometers, spectroscopic reflectometers, spectroscopic ellipsometers, polarized beam reflectometers, polarized beam spectroscopic reflectometers, scatterometers, spectroscopic scatterometers and optical CD measurement tools. Consequently, it is advantageous to provide processor 96 to analyze the output signals generated by the various detectors. These outputs correspond to changes in magnitude, changes in polarization state, changes in magnitude of polarized radiation and scatter measured at a plurality of wavelengths. The analysis protocols can treat the signals individually or in combination to evaluate the characteristics of a sample.

Examples of metrology tools having one or more of these measurement systems are described in U.S. Pat. Nos. 5,608,526 and 6,278,519, incorporated herein by reference. Systems of this type include at least one broadband light source generating a polychromatic probe beam which is directed to the surface of the sample. The reflected probe beam is measured to provide both reflectometry and ellipsometric information as a function of wavelength. U.S. Pat. No. 6,278,519 also illustrates the use of single wavelength lasers for measuring a sample.

It should be noted that reference sample 52 can be used to facilitate calibration of the wafer stage coordinates. In particular, the location of the edges of the reference sample can be accurately measured and compared to stage coordinates to calibrate measurement points with respect to a known coordinate system. In addition, measurement of the reference sample can also be used for focus adjustment in the Z-axis. In particular, the probe beam spot can be scanned over an edge of the reference sample while monitoring the reflected intensity. The distance over which the intensity moves from a minimum to a maximum gives a measure of spot size. This measurement is performed at a number of different z-positions, with the smallest measured spot size defining the focal plane.

While the preceding discussion of the preferred embodiments has focused on the use of a vacuum-chuck for clamping the wafer, the invention can also employ mechanical or electrostatic means to accomplish both the functions of wafer-clamping and holder actuation. Furthermore, mechanical and electrostatic means can be used in place of or in combination with the preferred vacuum-clamping embodiment. In systems employing vacuum-clamping of the wafer the addition of hydro-mechanical actuation may be accomplished cost-effectively. Particularly in those cases where the required hardware, e.g. vacuum systems, manifolds, pressure relief valves, sources of high-pressure gas, etc. are already incorporated in the existing wafer-clamping system. The ability to locate the reference sample within the wafer footprint also allows considerable reduction in the cost of the wafer translation systems, and the implementation of new, high-precision translation systems at a cost comparable to existing low-precision systems. These economic benefits accrue from the ability to utilize lower-cost, reduced-travel stages. For example, in the preferred embodiment of FIG. 3 the entire surface of a 300 mm diameter wafer can be measured using at least a 270° z-axis rotation stage in combination with two ±75 mm linear x and y translation stages.

What is claimed is:

1. A wafer support stage that permits the location of a reference sample within a stage area utilized for supporting a wafer, comprising:
   a platform for holding the wafer;
   a holder supporting a reference sample, said holder being located within a body of the platform at a location within the stage area utilized for supporting the wafer, said holder being movable between a retracted position where the reference sample is below the platform surface and an extended position; and
   a mechanism for moving the holder between the retracted and extended positions.

2. A wafer support stage according to claim 1, further comprising:
   a wafer motion system coupled to the platform for translating the platform.

3. A wafer support stage according to claim 1, wherein:
   the platform is capable of holding the wafer at a measurement position, and the reference sample is raised to be co-planar with the wafer measurement position when the holder is in the extendable position.

4. A wafer support stage according to claim 1, wherein:
   the platform is selected from the group consisting of mechanical, electrostatic and vacuum wafer chucking systems.

5. A wafer support stage according to claim 1, wherein:
   the mechanism for moving the holder between the retracted and extended positions employs one or more elements selected from the group consisting of mechanical, electro-mechanical, and hydraulic actuators.

6. A wafer support stage according to claim 1, wherein:
   the holder is a piston having a support surface for locating and holding the reference sample, said piston being contained within a housing, said piston being free to move between the retracted and extended positions.

7. A wafer support stage according to claim 6, wherein:
   the housing includes locating surfaces which limit the extent of the piston motion and determine the retracted and extended positions.

8. A wafer support stage according to claim 6, wherein:
   the holder further includes a member fixed to the outer surface of the piston for the purpose of forming a hydraulic seal between the piston and housing, thereby dividing the housing into upper and lower hydraulic chambers, thereby enabling hydraulic actuation of the piston motion within the housing through differential pressurization of the upper and lower hydraulic chambers.

9. A wafer support stage according to claim 8, wherein:
   the piston is spring loaded within the housing such that in the absence of differential pressurization of the upper and lower hydraulic chambers the piston locates in the retracted position.

10. A wafer support stage according to claim 8, wherein:
    the piston is spring loaded within the housing such that in the absence of differential pressurization of the upper and lower hydraulic chambers the piston locates in the extended position.

11. A wafer support stage according to claim 8, wherein:
    differential pressurization of the upper and lower hydraulic chambers is achieved by evacuating the lower hydraulic chamber.

12. A wafer support stage according to claim 8, wherein:
    differential pressurization of the upper and lower hydraulic chambers is achieved by pressurizing the lower hydraulic chamber.

13. A wafer support stage according to claim 8, wherein:
    differential pressurization of the upper and lower hydraulic chambers is achieved by evacuating the upper hydraulic chamber.

14. A wafer support stage according to claim 8, wherein:
differential pressurization of the upper and lower hydraulic chambers is achieved by pressurizing the upper hydraulic chamber.

15. A wafer support stage according to claim 8, wherein:
differential pressurization of the upper and lower hydraulic chambers is achieved by evacuating the upper hydraulic chamber and pressurizing the lower hydraulic chamber.

16. A wafer support stage according to claim 8, wherein:
differential pressurization of the upper and lower hydraulic chambers is achieved by evacuating the lower hydraulic chamber and pressurizing the upper hydraulic chamber.

17. A wafer support stage that permits the location of a reference sample within a stage area utilized for supporting a wafer, comprising:
a vacuum-chuck for holding a wafer;
a holder supporting a reference sample, said holder being located within the body of the vacuum-chuck at a location within the stage area utilized for supporting the wafer, said holder being movable between a retracted position where the reference sample is below the vacuum-chuck surface and an extended position where the reference sample is raised to be at least co-planar with the vacuum-chuck surface, said holder comprising:
a piston having a support surface for a reference sample located within and free to move within a housing, said housing containing locating surfaces that limit the range of the piston motion and establish the retracted and extended positions;
a member fixed to the surface of the piston said member forming a hydraulic seal between the piston and housing thereby dividing the housing into upper and lower hydraulic chambers and enabling hydraulic actuation of the piston by differential pressurization of said upper and lower hydraulic chambers; and
a hydro-mechanical actuation mechanism for moving the piston between the extended and retracted position, said actuation mechanism comprising:
a conduit connecting the upper hydraulic chamber to the surface of the vacuum-chuck;
a spring arranged to locate the piston in the retracted position in the absence of differential pressurization of the upper and lower hydraulic chambers and locate the piston in the extended position in the presence of differential pressurization of said upper and lower hydraulic chambers;
a gas manifold that connects the lower hydraulic chamber and vacuum-chuck to both a source of pressurized gas and a vacuum system; and
a check-valve arranged to inhibit differential pressurization of the upper and lower hydraulic chambers during manifold evacuation and enable differential pressurization of the upper and lower hydraulic chambers during manifold pressurization.

18. A wafer support stage according to claim 17, wherein:
a vacuum-chuck is utilized to holding the wafer in an optical metrology instrument selected from the group consisting of reflectometers, ellipsometers, spectroscopic reflectometers, spectroscopic ellipsometers, polarized beam spectroscopic reflectometers and optical CD measurement tools.

19. A wafer support stage that permits the location of a reference sample within a stage area utilized for wafer support, comprising:
a vacuum-chuck for holding the wafer;
a holder supporting a reference sample, said holder being located within the body of the vacuum-chuck at a location within the stage area utilized for wafer support, said holder being movable between a retracted position where the reference sample is below the vacuum-chuck surface and an extended position where the reference sample is raised to be at least partially above the vacuum-chuck surface;
a source of pressure in selective communication with the holder for biasing the holder into the extended position; and
a spring for urging the holder back to the retracted position.

20. A wafer support stage according to claim 19, further comprising:
a vacuum source in selective communication with the holder and also used to urge the holder back to the retracted position.

21. A wafer support stage according to claim 20, further comprising:
a valve for selectively coupling either the source of pressure or the vacuum source to the holder.

22. A wafer support stage according to claim 20, wherein:
said vacuum source is also coupled to the chuck for holding the wafer to the chuck.

23. A method for calibrating an optical metrology instrument, comprising the steps of:
placing a reference sample on a holder, the holder being located within a stage area of a platform utilized for supporting a wafer to be measured by the optical metrology instrument;
raising the reference sample such that a reference surface of the reference sample is located above a surface plane of the platform;
measuring the reference surface using the optical metrology instrument; and
lowering the reference sample below the surface plane such that the wafer to be measured can be placed on the stage area.

24. A method according to claim 23, further comprising:
adjusting the optical measurement instrument in response to the measurement of the reference sample.

25. A method according to claim 23, further comprising:
placing the wafer on the stage area; and
measuring the wafer surface with the optical metrology instrument.

26. A method according to claim 25, further comprising:
removing the wafer from the stage area; and
repeating the steps of raising, measuring, and lowering the reference sample after the step of measuring the wafer surface.

* * * * *